(12) United States Patent
Sampson

(10) Patent No.: US 7,563,223 B2
(45) Date of Patent: Jul. 21, 2009

(54) TUMESCENT SKIN SPACING METHOD

(75) Inventor: Russel M. Sampson, Palo Alto, CA (US)

(73) Assignee: Cytye Corporation, Marlborough, MA (US)

( * ) Notice: Subject to any disclaimer, the term of this patent is extended or adjusted under 35 U.S.C. 154(b) by 137 days.

(21) Appl. No.: 11/500,675

(22) Filed: Aug. 8, 2006

(65) Prior Publication Data
US 2007/0028932 A1 Feb. 8, 2007

(51) Int. Cl.
A61N 5/00 (2006.01)
A61B 19/00 (2006.01)

(52) U.S. Cl. .......................... 600/3; 128/898
(58) Field of Classification Search .............. 600/1–8, 600/547; 606/41; 128/898
See application file for complete search history.

(56) References Cited
U.S. PATENT DOCUMENTS

| | | | | |
|---|---|---|---|---|
| 5,472,416 A * | 12/1995 | Blugerman et al. | ........... | 604/28 |
| 5,527,273 A * | 6/1996 | Manna et al. | ................. | 604/22 |
| 5,884,631 A * | 3/1999 | Silberg | ....................... | 128/898 |
| 6,315,756 B1 * | 11/2001 | Tankovich | .................... | 604/35 |
| 6,535,759 B1 * | 3/2003 | Epstein et al. | ............... | 600/547 |
| 2003/0171701 A1 * | 9/2003 | Babaev | ........................... | 601/3 |
| 2004/0049251 A1 * | 3/2004 | Knowlton | .................... | 607/101 |
| 2005/0101860 A1 * | 5/2005 | Patrick et al. | ............... | 600/433 |
| 2005/0276864 A1 * | 12/2005 | LeTort | ......................... | 424/548 |

* cited by examiner

Primary Examiner—Samuel G Gilbert
(74) Attorney, Agent, or Firm—Lindsay McGuiness

(57) ABSTRACT

A method for increasing the distance between outer surface of tissue proximate to a surgical extraction site and a patient's sensitive body tissues comprising the infusion of a solution at a location of minimum distance between the extraction site and the sensitive body tissue until the accumulation of fluid distends the sensitive body tissue away from the extraction site.

20 Claims, 1 Drawing Sheet

TUMESCENT SKIN SPACING METHOD

FIELD OF THE INVENTION

A method is provided for increasing the distance between outer surface of the tissue proximate to a surgical extraction site and a patient's sensitive body tissues comprising the infusion of a solution at or near the a location of minimum distance between the extraction site and the sensitive body tissue until the accumulation of fluid distends the sensitive body tissue away from the extraction site.

A BACKGROUND OF THE INVENTION

Malignant tumors are often treated by surgical resection of the tumor to remove as much of the tumor as possible. Infiltration of the tumor cells into normal tissue surrounding the tumor, however, can limit the therapeutic value of surgical resection because the infiltration can be difficult or impossible to treat surgically. Radiation therapy can be used to supplement surgical resection by targeting the residual tumor margin after resection, with the goal of reducing its size or stabilizing it. Radiation therapy can be administered through one of several methods, or a combination of methods, including external-beam radiation, stereotactic radiosurgery, and permanent or temporary interstitial brachytherapy. The term "brachytherapy," as used herein, refers to radiation therapy delivered by a spatially confined radioactive material inserted into the body at or near a tumor or other proliferative tissue disease site. Owing to the proximity of the radiation source, brachytherapy offers the advantage of delivering a more localized dose to the target tissue region.

Brachytherapy can be performed by implanting radiation sources directly into the tissue to be treated. Brachytherapy is traditionally carried out using radioactive seeds such as $^{125}$I $^{103}$Pd seeds. These seeds, however, produce spatially inhomogeneous dose distributions. In order to achieve a minimum prescribed dosage throughout a target region of tissue, numerous radioactive seeds must be used, resulting in high doses being delivered in regions in close proximity to the seed (seeds which can cause radionecrosis in nearby healthy tissue) and relatively under-dosed spots between source positions.

One brachytherapy technique (i.e., intracavitary brachytherapy) uses a mechanical means of separating the radiation source from the surrounding tissues in order to reduce the amount of tissue exposed to the highest doses of radiation (e.g., the tissue that would have been in contact with the source). One such brachytherapy technique is balloon brachytherapy for post-lumpectomy patients. The current practice of balloon brachytherapy requires a minimum distance between the outer surface of the tissue proximate to a surgical extraction site (e.g., the lumpectomy cavity margins) and a patient's sensitive body tissues in order to avoid overexposure of such tissues.

Thus, it would be desirable to create a threshold distance between the outer surface of the tissue proximate to a surgical extraction site and a patient's skin in order to avoid overexposure of the skin during the brachytherapy procedure.

SUMMARY OF THE INVENTION

The present invention relates to apparatus and methods for increasing the distance between outer surface of the tissue proximate to a surgical extraction site and a patient's sensitive body tissues. More particularly, but not by way of limitation, the method of the present invention relates to a method for increasing the distance between the outer surface of a cavity left by the surgical excision of a tumor and a patient's skin.

In one embodiment of the present invention, a method for increasing the distance between a cavity left by surgical removal of a tumor and a patient's skin is presented, such method comprising inserting a device into the subcutaneous region between a cavity left by surgical removal of a tumor and a patient's skin, and the injection of a solution at the location of minimum distance between the cavity and the patient's skin until the accumulation of fluid distends the skin away from the cavity such that a threshold distance between the cavity and the patient's skin is obtained.

In another embodiment of the present invention, a method for increasing the distance between a cavity left by surgical removal of a tumor and a patient's skin is presented, such method comprising surgically removing at least a portion of a tumor thereby creating a cavity in a patient's remaining tissue, placing an inflatable treatment device in the cavity, the treatment device being connected by a catheter to an injection receptacle; implanting the injection receptacle subcutaneously; locating the injection receptacle by imaging the patient's body via X-ray, CT or other suitable technology; assessing the distance from the injection receptacle to the patient's skin; inserting a device into the subcutaneous region between the cavity left by surgical removal of a tumor and a patient's skin, and infusing a solution at the location of minimum distance between the cavity and the patient's skin until the accumulation of fluid distends the skin away from the cavity such that a threshold distance between the cavity and the patient's skin is obtained.

Numerous other objects, features and advantages of the present invention will be readily apparent to those skilled in the art upon a reading of the following disclosure when taken in conjunction with the accompanying drawing.

DEFINITIONS

Figure 1:
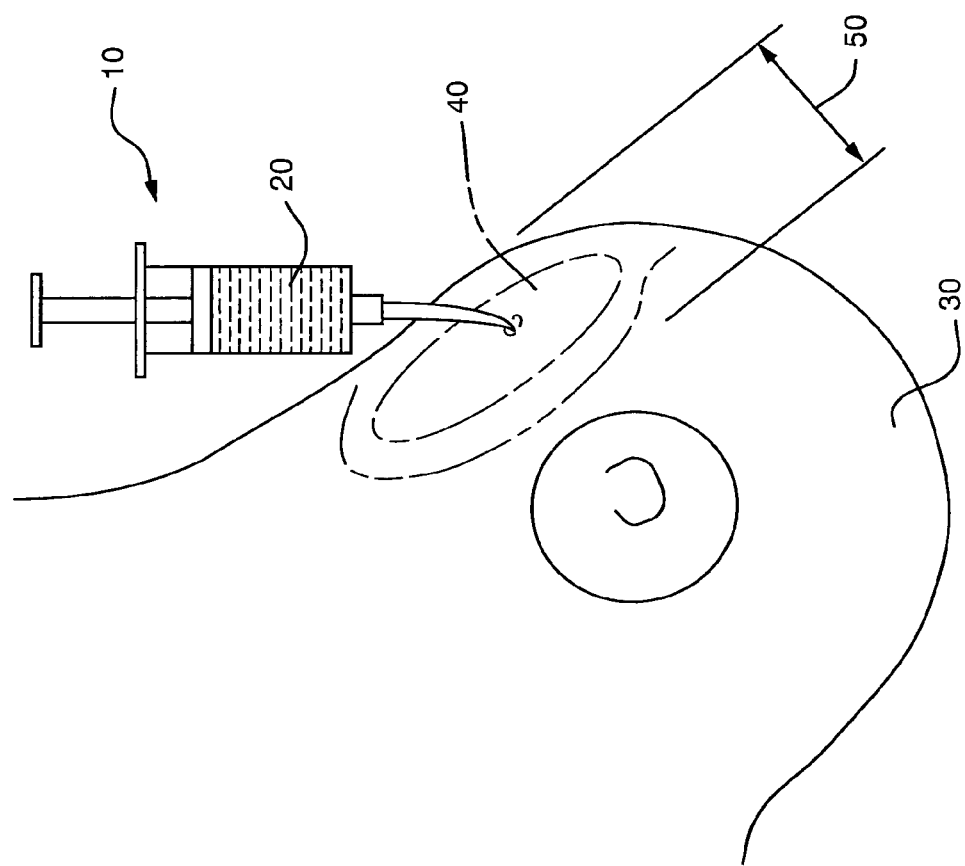
FIG. 1. is an illustration of the infusion of a solution subcutaneously to create a threshold distance between the between the outer edges of the cavity left by surgical removal of a tumor and a patient's skin.

As used herein, the following terms have the meanings ascribed to them unless specified otherwise.

The term "bio-absorbable and/or bio-degradable and/or bioerodible" refers to a composition that, when placed inside the body of an animal or a human, dissipates or diffuses into the surrounding body tissues.

The term "biocompatible" refers to a composition that is able to perform with an appropriate host response in a specific application (e.g., not having toxic or injurious effects on biological systems). Biocompatibility is generally established by government regulatory standards. Compositions that have not been tested against government standards may none the less be biocompatible if they can be tested and approved for use in an animal or human.

The term "biocompatible polymer" refers to any polymer selected from the group comprising alkyl celluloses, hydroxyalky methyl celluloses, hyaluronic acids, sodium chondroitin sulfates, polyacrylic acids, polyacrylamides, polycyanolacrylates, methyl methacrylate polymers, 2-hydroxyethyl methacrylate polymers, cyclodextrin, polydextrose, dextrans, gelatins, polygalacturonic acids, polyvinyl alcohols, polyvinyl pyrrolidones, polyalkylene glycols, polyethylene oxides, and the like. (see THE MERCK INDEX, 12th ed. 1996, Whitehouse Station, N.J.).

The term "bio-absorbable and/or bio-degradable and/or bioerodible polymer" refers to any polymer, which is preferably synthesized from monomers selected from the group consisting of D, L-lactide, D-lactide, L-lactide, D, L-lactic acid, D-lactic acid, L-lactic acid, glycolide, glycolic acid, s-caprolactone, s-hydroxy hexanoic acid, γ-butyrolactone, y-hydroxy butyric acid, 8-valerolactone, 8-hydroxy valeric acid, hydrooxybutyric acids, malic acid, polylactides, polyglycolides, polycaprolactones, polyorthoesters, polyetheresters, polyphosphazines, polyanhydrides, polyesteramides, polyalkyl cyanoacrylates, and blends and copolymers thereof. Examples of suitable biodegradable polyesters are disclosed in U.S. Pat. Nos. 5,324,519; 4,938,763; 5,702,716; 5,744,153; 5,990,194; and 6,773,714.

The term "gel" refers to a composition with gelatinous, jelly-like, or colloidal properties that includes both a semisolid gel state and a high viscosity state that exists when gelation conditions are met.

The term "polymeric gel" means any polymer, copolymer, block copolymer and the like that congeals or precipitatively solidifies when administered within a biological environment, but may be a liquid under conditions not present in that environment The term "polymer solution" means an aqueous solution and the like, when used in reference to a biodegradable polymer or block copolymer contained in such solution, shall mean a water based solution having a gel forming block copolymer dissolved therein at a functional concentration, and maintained at a temperature of non-gelation temperatures such that gel formation does not occur.

The term "reverse thermal gelation" refers to the phenomena whereby a solution of a polymer or block copolymer spontaneously increases in viscosity, and in many instances transforms into a semisolid gel, as the temperature of the solution is increased above the gelation temperature of the polymer.

The term "thermosensitive and/or thermoplastic polymeric gel" means any polymeric gel that, depending on temperature, may exist in liquid state or a gel state.

DETAILED DESCRIPTION OF THE INVENTION

Brachytherapy refers to the technique of implanting radioactive sources directly into a specific part of the body. Radioactive seeds or sources are placed in or near the tumor itself, giving a high radiation dose to the tumor while reducing the radiation exposure in the surrounding healthy tissues. Alternatively, the radiation source(s) can be implanted in the surgical resection cavity following tumor resection or debulking, specifically to irradiate the resection cavity margins for improvement in local tumor recurrence control. These sources may be temporarily or permanently implanted. Temporary brachytherapy implants usually involve the insertion of numerous discrete radiation sources throughout the target volume (the tissue for which radiation therapy is beneficial). These sources are contained in catheters threaded through the target volume and are removed, along with the brachytherapy sources, after the desired radiation dose has been delivered (usually in 3-6 days). These implants are referred to as temporary Low Dose Rate (LDR) implants. Permanent implants, such as permanent prostate implants, are left in the tissues and the radiation decays over time. Lastly, there are brachytherapy implants where an applicator system is implanted into the target volume and the radiation source(s) is deployed into the applicator system for a short period of time (usually seconds to minutes) and then removed. The source deployment may occur once or several times, a process referred to as fractionated High Dose Rate (HDR) brachytherapy. The rationale for using brachytherapy is that it can deliver radiation to a small area while increasingly sparing the amount of normal tissue that is irradiated. Brachytherapy can be used to treat many different types of tumors such as, for example, tumors of the prostate, breast, lung, esophagus, cervix, uterus, liver, neck, nasopharnx, brain, spine, oral cavity, as well as other soft tissue sarcomas.

Temporary brachytherapy can be delivered in one of two ways; multi-catheter brachytherapy and balloon brachytherapy. Multi-catheter brachytherapy consists of implanting multiple (up to 30) catheters (tubes) in or near a tumor. After placement, a radioactive seed is delivered into each catheter to treat the target area. Balloon catheter brachytherapy is an intracavitary balloon radiation device to treat early-stage cancers. During a lumpectomy or shortly after, a single balloon catheter is inserted through a small incision into the cavity created by the surgical removal of the tumor. The balloon-tipped end is inflated with sterile fluid to fill the cavity, and the exit site is dressed. The patient then returns for radiation therapy, most likely receiving two radiation treatments daily for five days. Standard gamma radiation is provided by a tiny radioactive bead about twice the size of a pinhead attached to the end of a wire. The end of the catheter is attached to a High Dose Rate Afterloader, a device that houses a radioactive source and mechanically delivers radiation to the body. The radiation source exits from the Afterloader and slides up the catheter into the center of the inflated balloon, stopping at multiple positions to deliver various levels of radiation from inside the balloon. After the final treatment session, the balloon is deflated, and the catheter is removed.

One particular promising application of balloon catheter brachytherapy has been in the treatment of breast cancer (see Dowlat K, et al. *Early experience with balloon brachytherapy for breast cancer. Arch Surg.* 139: 603-608; 2004; Arthur D W. *Accelerated Partial Breast Irradiation: A Change in Treatment Paradigm for Early Stage Breast Cancer. J Surg Oncol.* 84: 185-191; 2003). Balloon catheter brachytherapy facilitates the delivery of partial breast irradiation following lumpectomy for breast cancer. The balloon catheter is inserted into the surgical cavity through a separate pathway created by a trocar, or via the lumpectomy scar. The balloon end of the catheter is inflated with saline and contrast agent to allow the surrounding tissue to conform to the balloon, the exit site is dressed, and the patient is sent home. Once the patient has sufficiently recovered from surgery (typically the next day), she is referred to her radiation oncologist for CT of the balloon in the breast and treatment planning. During therapy, a $^{192}$Ir seed (attached to a high-dose rate [HDR] remote afterloader) is inserted into the inflated balloon for a short duration (typically less than 10 minutes). When used as primary radiation therapy, 2 treatments are administered per day, for 5 days, to deliver the prescribed radiation dose (typically 34 Gy delivered to a distance of 1.0 cm from the balloon's surface). When used as a boost with external beam radiation, a typical prescription requires treatment for 1-2 days. After radiation therapy is concluded, the balloon is deflated and the catheter is removed.

During the balloon brachytherapy procedure, a minimum distance between the balloon's surface and the patient's skin must be maintained in order to avoid adverse cosmetic effects, temporary toxicity and/or permanent toxicity to the skin tissue. For example, the Mammosite® brachytherapy procedure for breast tumors (Cytyc Corporation, Marlborough, Mass.) is contraindicated for less than the minimum prescribed distance of 5 mm between the outer surface of the breast tissue proximate to a lumpectomy site and a patient's skin. It is desirable, to decrease the potential for adverse skin reactions, to maintain as much distance between the skin and the balloon surface as is feasible.

Sparing sensitive tissues (e.g., in the example above, the skin) is not limited to the skin, but can apply to a variety of radiation sensitive, normal tissues, that may be in close proximity to the brachytherapy implant site.

There have been numerous mechanical devices that have been proposed to increase the distance between a radioactive source and a patient's sensitive tissues, however, such devices have proven to be either too complex and/or too costly. As such, it would be desirable to create a low cost, low complexity system which would create a threshold distance between a balloon's surface and a patient's sensitive tissues.

Accordingly, the method of the present invention relates to providing a system for increasing the distance between the outer surface of the tissue proximate to a surgical extraction site and a patient's sensitive body tissues.

In general, a surgical extraction site according to the present invention includes, but is not limited to, the cavity left after tumor resection. As used herein, the term "tumor" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cyst. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The present method can also be used against nonsmall cell, squamous, liver, renal, adrenal, stomach, esophageal, oral and mucosal tumors, melanomas (including amelanotic subtypes), eye tumors (retinoblastoma), muscle carcinomas (rhabdomyosarcoma), endometrial tumors, bladder cancer, pancreatic cancer, sarcomas and testicular cancer as well as against tumors of the central nervous system, such as neuroblastomas and brain tumors, and tumors of the bone such as osteogenic and Ewing's sarcoma. Exemplary tumors of the present invention include those forming from tissue of the cervix, lung, prostate, breast, head and neck, colon and ovary.

For the purposes of the present invention, sensitive tissues include epithelia, mucous membranes, and tissues of the pelvic, abdominal, chest, and thyroid gland areas. More specifically, the present invention can be used to protect tissues of the pancreas, kidney, heart, brain, colon, liver, lung, oesophagus, ovary, uterus, cervix, bladder as well as the GI tract (e.g., stomach, intestines, and colon), immune system, hematopoietic system (e.g., bone marrow) and bone.

In one embodiment of the present invention, a method for increasing the distance between a cavity left by surgical removal of a tumor and a patient's skin is presented, such method comprising inserting a device into the subcutaneous region between a cavity left by surgical removal of a tumor and a patient's skin, and the injection of a solution at the location of minimum distance between the cavity and the patient's skin until the accumulation of fluid distends the skin away from the cavity such that a threshold distance between the cavity and the patient's skin is obtained.

In another embodiment of the present invention, a method for increasing the distance between the outer surface of a lumpectomy and a patient's skin is presented, such method comprising inserting a device into the subcutaneous region between a cavity left by the lumpectomy and a patient's skin, and the injection of a solution at the location of minimum distance between the cavity and the patient's skin until the accumulation of fluid distends the skin away from the cavity such that a threshold distance between the cavity and the patient's skin is obtained.

In yet another embodiment of the present invention, a method for increasing the distance between a cavity left by surgical removal of a tumor and a patient's skin is presented, such method comprising surgically removing at least a portion of a tumor thereby creating a cavity in a patient's remaining tissue, placing an inflatable treatment device in the cavity, the treatment device being connected by a catheter to an injection receptacle; implanting the injection receptacle subcutaneously locating the injection receptacle by imaging the patient's body; assessing the distance from the injection receptacle to the patient's skin; inserting a device into the subcutaneous region between the cavity left by surgical removal of a tumor and a patient's skin, and infusing a solution at the location of minimum distance between the cavity and the patient's skin until the accumulation of fluid distends the skin away from the cavity such that a threshold distance between the cavity and the patient's skin is obtained.

In one embodiment of the present invention, the method of the present invention relates to the injection of a solution consisting of a bio-absorbable polymer at the location of minimum distance between a lumpectomy cavity and the skin of the breast until the accumulation of the solution distends the skin away from the cavity such that a threshold distance between the cavity and the skin of the breast is obtained. Once infused subcutaneously, the polymer solution undergoes a gel transition forming in situ formed edema in the breast. The polymer solution may be composed of a biodegradable thermoplastic polymer or copolymer in combination with a suitable polar aprotic solvent. The biodegradable thermoplastic polyesters or copolymers are substantially insoluble in water and body fluid, biocompatible, and biodegradable and/or bioerodible within the body of an animal. The composition is biocompatible and the polymer matrix does not cause substantial tissue irritation or necrosis at the injection site.

FIG. 1 illustrates a hypodermic needle 10 injecting a solution 20 subcutaneously into the breast of a patient 30. The injection of solution is at the location of minimum distance between a lumpectomy cavity and the skin of the breast until the accumulation of the solution forms an edema 40 which distends the skin away from the cavity such that a threshold distance 50 between the cavity and the skin of the breast is obtained.

In general, the minimum threshold distance may be defined as the minimum necessary distance between the outer surface of the tissue proximate to a surgical extraction site and a patient's sensitive body tissues in order to avoid toxicity to the sensitive tissues during a brachytherapy procedure. Preferably, the minimum threshold distance is greater than 5 millimeters.

In general, the polymer solution can be a liquid or a gel, suitable for injection in a patient (e.g., human). As used herein, "solution" refers to the ability of the polymer to be injected through a medium (e.g., syringe) into the body of a patient. For example, the composition can be injected, with the use of a syringe, beneath the skin of a patient. The ability of the solution to be injected into a patient will typically depend upon the viscosity of the solution. The solution will therefore have a suitable viscosity, such that the solution can be forced through the medium (e.g., syringe) into the body of a patient. Once in the body, the solution coagulates into a solid. One type of solution includes a nonreactive thermoplastic polymer or copolymer dissolved in a body fluid-dispersible solvent. This polymeric solution is placed into the body where the polymer congeals or precipitatively solidifies upon the dissipation or diffusion of the solvent into the surrounding body tissues.

Any suitable thermoplastic polymers can be employed, provided the thermoplastic polymer is at least substantially insoluble in aqueous medium or body fluid. When cooled below the gelation temperature, the gel spontaneously reverses to reform the lower viscosity solution. This cycling between the solution and the gel may be repeated because the sol/gel transition does not involve any change in the chemical composition of the polymer system. All interactions to create the gel are physical in nature and do not involve the formation or breaking of covalent bonds.

The composition is useful for partially or completely filling a subcutaneous space with a composition for increasing the distance between a cavity left by surgical removal of a tumor and a patient's skin. Although not a necessity, it is preferable that the composition be bio-absorbable. For the composition to be bio-absorbable, all parts of the composition are bio-absorbable, thus including the polymer, the solvent and the resulting gel after a gel transition. These biodegradable polymers are gradually degraded by enzymatic or non-enzymatic hydrolysis in aqueous or physiological environments. The degradation products are polyethylene glycol, lactic acid and glycolic acid. These compounds are relatively innocuous and can easily be excreted or absorbed by the biological system. Any additives must be bio-absorbable as well. The bio-absorbable composition should also be nontoxic, including also that the polymer, solvent, resulting gel and any additives are also nontoxic.

Alternatively, the gel transition of the solution injected into a patient can occur as a result of in situ cross linking of the gel composition. Such a cross linkable gel composition can comprise cross linkable free radicals, or cationic/anionic cross linkable moieties. For example, the gel composition can comprise cyanoacrylates, or FocalGel™. The cross linking reaction can be activated by a chemical reaction, a change in temperature, or the application of energy (e.g., light). For example, the cross linking can be activated by an application of an energy source selected from the group consisting of radiation, magnetic, microwave, ultrasonic, ultra-violet, radio frequency, visible light, and heat. These energy sources can be applied to the polymer or composition just prior to administration into the patient, or can be applied during or just after the composition is administered. The energy sources are derived from standard sources for the energy applied.

Usually, the composition is liquid before delivery to a patient and undergoes a gel transition inside the target tissue within about 30 minutes of delivery of the composition. The gel transition time can be in a range from about 0 to 2 minutes, from about 2 to 5 minutes, from about 6 to 10 minutes, from about 11 to 15 minutes, from about 16 to 20 minutes, from about 21 to 25 minutes, or from about 26 to 30 minutes. The gel may begin to transition slowly, so that a few seconds after the polymer has been exposed to a condition which begins the gelling process, the gelling process can begin, but gelling may not be completed right away. Delivery may be facilitated using the polymer in a liquid form, or a slightly viscous form (i.e., when the gelling is beginning to take place). The gel transition can also begin as soon as about a minute after delivery of the first amount of gel composition to the patient. Preferably the gel transition will not begin until the earliest delivered aliquot of the gel composition has been delivered. Alternatively, where delivery is facilitated using a slightly or mildly viscous polymer, the gel transition is beginning sooner than before all or part is delivered, but the polymer is still of a sufficient consistency that delivery can be accomplished. Thus, it is preferable that the gel composition undergoes a gel transition after the first-delivered amounts of the composition have had time to infuse into the target tissue. The time needed to have the gel composition remain liquid will vary depending on such parameters, for example, as the flow rate of the gel composition, the speed of gelation once the gel transition begins, the cause of the gel transition, the depth of penetration of the delivery tool into the catheter, the lumen size of the delivery tool, and the proficiency of the practitioner delivering the gel.

A syringe or other infusion device may directly infuse the liquid into the target tissue (e.g., breast), or if attached to the delivery tool, a syringe may infuse the liquid into a delivery lumen of the tool. An appropriate preparation for a temperature sensitive polymer in order to provide an appropriate window for administration of the gel and to ensure gelation once inside the patient (and not before) may be cooling the liquid polymer to a temperature below gelation temperature. For example, the polymer may be cooled before it is administered by being placed on ice, or refrigerated. In addition, an administration tool may be cooled, and/or the injection site itself may be iced or wrapped in a cooling cloth that lowers the skin temperature. Once administered, the body provides a source of warming and thus allows for gelation. Other measures may be taken for polymers that are not temperature sensitive but which respond to other changes that can be controlled just prior to administration in order to maximize the opportunity for the polymer to penetrate the ductal architecture before gelation occurs.

If too much time passes before the gel transition occurs, the procedure runs the risk of having the solvent diffuse and/or the conditions inside the tissue and with the liquid polymer to change to a point that alters any optimal gel transition or the ultimate consistency of the gel. In addition, because the delivery of the gel composition to a patient is for the purpose of performing a brachytherapy procedure, an optimal time period before the gel transition is complete is approximately a maximum of 30 minutes. Also, if too much time passes before the gel transition, any additives added to the solution may diffuse into the surrounding tissue and lose their effectiveness for their intended purpose. For example, where an additive is one that can be detected in the gel, and is required to locate the gel, if that additive has a chance to diffuse into surrounding tissue before gel transition occurs, the effectiveness of that additive is greatly reduced.

Additionally, the gel can harden to various consistencies, provided it becomes less liquid and more viscous once it undergoes a gel transition. Thus, the gel can be, for example, less hard than the surrounding tissue, about the same consistency as the surrounding tissue, somewhat stiffer or harder than the surrounding tissue, or much stiffer and harder than the surrounding tissue. The main objective is to provide a gel-filled pocket within the patient's tissue with sufficient stiffness that it creates the necessary threshold distance between the outer surface of the tissue proximate to a surgical extraction site and a patient's sensitive body tissues without causing discomfort to the patient. The gel hardness may also be considered in more absolute and less comparative terms, so that an essentially viscous gel may work for the purposes of the invention and a much harder gel may also work.

The gel composition in the target tissue after gel transition can be distinguishable from surrounding tissue. The composition that has undergone its gel transition can be distinguishable by any factor that can distinguish it from tissue, or any number or combination of these factors. The gel might be colorless, for example, but hardened, and by hardening inside the patient's tissue, might make the gel distinguishable from the surrounding tissue by virtue of the different density and tensile strength of the gel versus the surrounding tissue. Thus, the stiffness of the gel alone can make the gel detectable to a practitioner.

Other mechanisms of making the gel inside the patient's tissue distinguishable from tissue include having the gel contain a color different than the surrounding tissue and which is visible to the naked eye, or other wise visible with special light. For example, the gel can be pink, green, blue, yellow, purple, or any other color available in a dye that can be added to the gel composition before delivery to the patient's tissue. Other mechanisms of making the gel distinguishable from tissue can include placing additives in the gel that can be detected by nonvisual means. Such nonvisual means can include, e.g. detection by special sensors capable of sensing the particular additive in the gel that is not present in the surrounding tissue. Thus, as the polymer solution is being delivered to the patient's tissue and the gel transition has occurring, a polymer solution having such additives can be "read" and detected by using the sensor appropriate for the additive.

Although it is possible that the polymer solution may have very few or no additives, and by virtue of hardening alone can be used to detect the gel, it is more likely that at least one if not more than one other additives can be added to the composition to aid in the detection of the gel inside the patient's tissue. The additive can be capable of detection by a special sensor or machine or other mechanism that is sensitive to the presence of such an additive and which can detect material that has the additive and distinguish such material from other material not containing the particular additive. The additive can be a fluorescent agent, including e.g. any commercially available fluorescent agent that is biocompatible. Some exemplary fluorescent agents include, e.g. fluorescein, rhodamine or indocyanine green, but others also exist and may be available from such companies as Molecular Probes located at Eugene, Ore., or Promega Corp., located at Madison, Wis., and other companies that supply reagents for biomedical scientific research purposes. Other fluorescent dyes that may be adaptable to use in a gel in a breast duct include green fluorescent protein (GFP) or blue fluorescent protein (BFP).

The additive can also be an agent detectable by other means, including, e.g. a radiographic contrast agent, a radionuclide, a ferromagnetic material, a sonographically reflective material, a thermographically reflective material, an impedance altering molecule, a radioactive agent, and an agent detectable by infrared sensor. An agent detectable by infrared sensor is available from HotHands/Johnston Sales Co., Little Rock, Ark. (phone 501-661-1199).

More than one additive can be used to make the gel-filled duct detectable, each additive perhaps performing a slightly different purpose in the process. For example, an additive that makes the gel visible to the naked eye or to the naked eye with the aide of a special light (e.g. UV light) can be used so that a practitioner can see at a glance where the duct gel is and how much solution has been injected into the patient. However, another additive can also be added in order to precisely determine the increased distance between the outer surface of the tissue proximate to a surgical extraction site and a patient's sensitive body tissues.

Additives in addition to detection or identification additives may be placed in the gel for mapping the ducts in the breast, including, e.g. therapeutic additives. The therapeutic additives may be, e.g. additives to aid in pain management or healing after surgery or radiation treatment. The additives may be either retained in the biodegradable gel, or be permitted by the gel matrix and gel transition chemistry to seep from the gel and into surrounding tissue. For example, lidocaine or other local anesthetics may be incorporated into the polymer solution to provide a measure of comfort to the patient. Also, additives may be added to the gel composition in order to provide additional protection for the patient's sensitive tissues from harmful radiation. For example, protective additives such as organic compositions (e.g., proteins) and/or inorganic compositions (e.g., metals) may be suspended within the polymer solution which effectively absorb or deflect harmful radiation from a patient's sensitive tissues. The addition of such protective additives may also directly impact upon the minimum threshold distance.

In general, the polymer composition that is useful for partially or completely filling a subcutaneous space for increasing the distance between a cavity left by surgical removal of a tumor and a patient's skin is bio-absorbable. For the composition to be bio-absorbable, all parts of the composition are bio-absorbable, thus including the polymer, the solvent and the resulting gel after a gel transition as well as any additives. The period of time over which the gel composition is absorbed into the patient's tissues is important. It is preferable that the gel composition is not substantially absorbed into the surrounding tissues until the patient has finished his/her radiation therapy. Thus, in a preferred embodiment of the present invention the gel composition formed by the injection or infusion of a polymer solution into a patient's tissue between a cavity left by surgical removal of a tumor and a patient's skin is not substantially absorbed into the surrounding tissues for at least one week, and preferably a minimum of two to three weeks post injection. Although it is preferable that the resulting gel composition be bio-absorbable, it is recognized that certain gels may not be bio-absorbable or may be only bio-absorbable over an extended period of time. As such, it may be necessary to have the non-absorbable gel removed from the patient via a surgical procedure.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this inven-

The invention claimed is:

1. A method for increasing the distance between the outer surface of tissue proximate to a surgical extraction site and sensitive body tissue comprising: infusing a solution directly into the tissue at or near a location of minimum distance between said outer surface of the tissue and said sensitive body tissue until the accumulation of fluid distends said sensitive body tissue away from said outer surface of the tissue.

2. The method of claim 1, wherein said sensitive body tissue is skin.

3. The method of claim 1, wherein said surgical extraction site is a lumpectomy cavity.

4. The method of claim 1, wherein said solution contains a polymer that can undergo a gel transition.

5. The method of claim 4, wherein said polymer is bio-absorbable.

6. The method of claim 4, wherein said solution further comprises additives to aid in the detection of said gel.

7. The method of claim 1, wherein said solution contains an anesthetic.

8. A method for increasing the distance between a cavity left by surgical removal of a tumor and a patient's skin comprising:
   (a) inserting a device into the subcutaneous region between a cavity left by surgical removal of a tumor and a patient's skin; and
   (b) injecting a solution directly into the tissue at or near the location of minimum distance between said cavity and said patient's skin until the accumulation of fluid distends the skin away from said cavity such that a threshold distance between the cavity and the patient's skin is obtained.

9. The method of claim 8, wherein said threshold distance is greater than 5 millimeters.

10. The method of claim 8, wherein said tumor is a breast tumor.

11. The method of claim 8, wherein said solution contains a polymer that can undergo a gel transition.

12. The method of claim 11, wherein said polymer is bio-absorbable.

13. The method of claim 11, wherein said solution further comprises additives to aid in the detection of said gel.

14. The method of claim 8, wherein said solution contains an anesthetic.

15. A method for increasing the distance between a cavity left by surgical removal of a tumor and a patient's skin comprising:
   (a) surgically removing at least a portion of a tumor thereby creating a cavity in a patients remaining tissue;
   (b) placing an inflatable treatment device in said cavity, said treatment device being connected by a catheter to an injection receptacle;
   (c) implanting said injection receptacle subcutaneously;
   (d) locating said injection receptacle by imaging the patient's body;
   (e) assessing the distance from said injection receptacle to the patient's skin;
   (f) inserting a device into the subcutaneous region between a cavity left by surgical removal of a tumor and a patient's skin; and
   (g) infusing a solution directly into the tissue at the location of minimum distance between said cavity and said patient's skin until the accumulation of fluid distends the skin away from said cavity such that a threshold distance between the cavity and the patient's skin is obtained.

16. The method of claim 15, wherein said an inflatable treatment device is a balloon brachytherapy catheter.

17. The method of claim 15, wherein said solution contains a polymer that can undergo a gel transition.

18. The method of claim 17, wherein said polymer is bio-absorbable.

19. The method of claim 17, wherein said solution further comprises additives to aid in the detection of said gel.

20. The method of claim 15, wherein said solution contains an anesthetic.

* * * * *